United States Patent [19]

Imahori et al.

[11] Patent Number: 4,554,253

[45] Date of Patent: Nov. 19, 1985

[54] APPARATUS FOR SYNTHESIZING ADENOSINE-5′-TRIPHOSPHATE

[75] Inventors: Kazutomo Imahori, No. 2-25-23, Kakinokisaka, Meguro-ku, Tokyo; Tatsuo Iwasaki, Kyoto; Hiroshi Nakajima, Kyoto; Hitoshi Kondo, Kyoto; Isao Tomioka, Kyoto; Masaru Kashima, Osaka; Toshihiko Tsukamoto, Kyoto, all of Japan

[73] Assignees: Kazutomo Imahori; Rikagaku Kenkyusho; Unitika Ltd., all of Japan

[21] Appl. No.: 461,309

[22] Filed: Jan. 26, 1983

[30] Foreign Application Priority Data

Jan. 26, 1982 [JP] Japan ................................. 57-10338

[51] Int. Cl.$^4$ ............................................. C12M 1/40
[52] U.S. Cl. ..................................... 435/288; 435/89; 435/92; 435/289; 435/290; 435/291
[58] Field of Search ................. 435/288, 289, 291, 92, 435/89

[56] References Cited

U.S. PATENT DOCUMENTS

| | | | |
|---|---|---|---|
| 2,174,475 | 9/1939 | Ostern et al. | 435/92 |
| 3,769,165 | 10/1973 | Nakayama | 435/92 |
| 3,926,737 | 12/1975 | Wilson et al. | 435/289 |
| 3,937,615 | 2/1976 | Clack et al. | 435/289 |
| 4,048,018 | 9/1977 | Coughlin et al. | 435/288 |
| 4,164,444 | 8/1979 | Whitesides et al. | 435/92 |
| 4,442,216 | 4/1984 | Harvey et al. | 435/288 |

Primary Examiner—Sam Rosen
Attorney, Agent, or Firm—Sughrue, Mion, Zinn, Macpeak, and Seas

[57] ABSTRACT

An apparatus for converting into ATP which comprises an enzyme reactor, a source of AMP supply, a source of phosphoric acid donator supply, variable fluid sending apparatus, an automatic sampling apparatus and an analyzing apparatus for the reacting solution, an arithmetic control apparatus, and a recovery apparatus. According to this apparatus, conversion from AMP or ADP into ATP can be effectively carried out and ATP conversion can be kept at substantial 100% over a long period of time. The device makes it possible for ATP to be used more and more in future as an energy source for bioreactors and as medicines because the ATP will be more readily available and less expensive.

8 Claims, 2 Drawing Figures

APPARATUS FOR SYNTHESIZING ADENOSINE-5'-TRIPHOSPHATE

FIELD OF THE INVENTION

The present invention relates to an apparatus for converting adenosine-5'-monophosphate or adenosine-5'-diphosphate into adenosine-5'-triphosphate.

BACKGROUND OF THE INVENTION

In recent years, so-called bioreactors wherein the same biosynthesis as that in the living body is industrially carried out outside the living body have been studied. Among biochemical reactions to be adopted for such devices, there are many cases of using adenosine-5'-triphosphate (hereinafter referred to as ATP) as an energy source. In this case, ATP operates as an energy source for chemical reactions and is converted into adenosine-5'-monophosphate (hereinafter referred to as AMP) or adenosine-5'diphosphate (hereinafter referred to as ADP). Accordingly, if ATP is converted from AMP or ADP at a moderate price, the bioreactor becomes more advantageous economically because it is not necessary to waste expensive ATP. However, hitherto, ATP has been obtained by extracting it from animal tissues or by a batch process such as a fermentation process utilizing microorganisms. Consequently, ATP is inevitably very expensive, because the production efficiency is inferior or purity is low and a complicated purifying step is required because of culture residues as described in R. S. Langer, B. K. Hamilton, C. R. Gardner, M. C. Archer and C. K. Colton, *AIChE J.*, 22, 1079 (1976), and Japanese Patent Application (OPI) Nos. 136591/78 and 24036/80 ( the term "OPI" as used herein refers to a "published unexamined Japanese patent application "), etc. This fact is an obstacle with respect to the practical application of bioreactors. Accordingly, there has been a strong desire to develop a new technique for converting into ATP having a high purity at a moderate price.

In view of such requirement, attempts have been made at utilizing ATP conversion enzymes. For example, Langer et al. reported a process for converting AMP into ATP by means of adenylate kinase in rabbit muscles and acetate kinase in Escherichia coli in R. S. Langer, B. K. Hamilton, C. R. Gardner, M. C. Archer and C. K. Colton, *AIChE J.*, 22, 1079 (1976) and U.S. Pat. No. 4,164,444. Further, it has been reported to convert adenosine into ATP using adenosine kinase in addition to the above-described two kinds of conversion enzyme (R. L. Baughn, O. Adalsteinsson and G. M. Whitesides, *J. Am. Chem. Soc.*, 100, 304 (1978)). Further, reports have been written with respect to the use of immobilized enzymes, but the stability of such with the passage of time is remarkably inferior (G. M. Whitesides, A. Chmurny, P. Garrett, A. Lamotte and C. K. Colton, *Enzyme Eng.*, 2, 217 (1974)). The process of using such enzymes is not suitable industrially, because it is not a process for continuously converting into ATP efficiently over a long period of time by a systematic method. Accordingly, there has been a need to develop an apparatus for constantly, effectively and stably converting into ATP over a long period of time.

SUMMARY OF THE INVENTION

An object of the present invention is to provide an apparatus for constantly, effectively and stably converting into ATP over a long period of time.

As a result of ernest studies, the present inventors have found that all the above-described objects can be attained by using an apparatus using conversion enzymes produced from microorganisms having an optimum growth temperature of 50° C. to 85° C.

Namely, the present invention relates to an apparatus for converting into ATP which comprises (a) an enzyme reactor including an enzyme which converts AMP into ADP and has been produced from microorganisms having an optimum growth temperature of 50° C. to 85° C. and an enzyme which converts ADP into ATP and has been produced from microorganisms having an optimum growth temperature of 50° C. to 85° C. (an enzyme reactor), (b) a source of AMP, (c) a source of phosphoric acid donator supply for converting AMP into ADP and a source of phosphoric acid donator supply for converting ADP into ATP (a source of phosphoric acid donator), (d) variable fluid sending apparatus which are arranged and connected so that AMP and each of the above-described phosphoric acid donator are fed from each of said sources of supply (b) and (c) to an end of said enzyme reactor at controlled amounts of flowing to cause enzymic reactions and a reacting solution is flown out continuously from the other end, (e) an automatic sampling apparatus and (f) an analyzing apparatus for the reaction solution within the enzyme reactor which are arranged and connected so as to automatically analyze ATP, ADP and AMP in the reacting solution flown out from said enzyme reactor, (g) an arithmetical control apparatus which is arranged and connected so as to control the amount of flowing in at least one of said variable fluid sending apparatus, by which arithmetical operation is carried out on the basis of data signals received from said analyzing apparatus and signals of the prescribed values previously fed so as to keep the ATP conversion in said enzyme reactor or the ATP concentration in the outlet of said reactor at a previously prescribed value, and (h) a recovery apparatus for recovering the reacting solution flown out from said enzyme reactor; and an apparatus for converting into ATP which comprises (a) an enzyme reactor including an enzyme which converts ADP into ATP and has been produced from microorganisms having an optimum growth temperature of 50° C. to 85° C. (an enzyme reactor), (b) a source of ADP, (c) a source of phosphoric acid donator supply for converting ADP into ATP, (d) variable fluid sending apparatus which are arranged and connected so that ADP and the above-described phosphoric acid donator are fed from each of said source of supply (b) and (c) to an end of said enzyme reactor at controlled amounts of flowing to cause an enzymic reaction and a reacting solution is flown out continuously from the other end, (e) an automatic sampling apparatus and (f) an analyzing apparatus for the reaction solution within the enzyme reactor which are arranged and connected so as to automatically analyze ATP, ADP and AMP in the reacting solution flown out from said enzyme reactor, (g) an arithmetical control apparatus which is arranged and connected so as to control the amount of flowing in at least one of said variable fluid sending apparatus, by which arithmetical operation is carried out on the basis of data signals received from said analyzing apparatus and signals of the prescribed values previously fed so as to keep the ATP conversion in said enzyme reactor or the ATP concentration in the outlet of said reactor at a previously prescribed value, and (h) a recovery apparatus for recovering the reacting solution flown out from said enzyme reactor.

In the apparatus of the present invention, it is possible to efficiently convert AMP or ADP into ATP while maintaining the ATP conversion at substantial 100% over a long period of time.

DETAILED DESCRIPTION OF THE INVENTION

Figure 1:
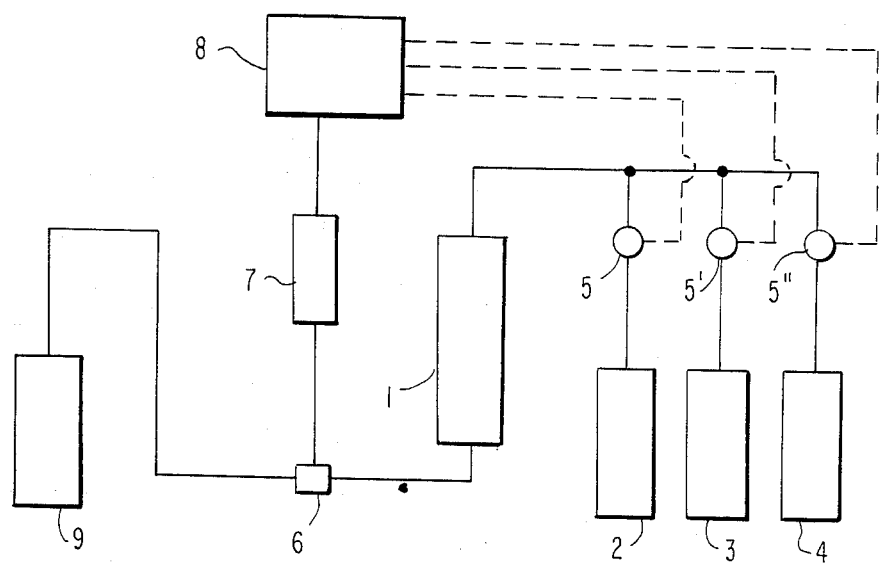
FIG. 1 is a schematic view showing the basic constitution of an embodiment of the present invention.

In the following, embodiments of the present invention are illustrated with reference to the drawings FIG. 1 is a schematic view which indicates the basic constitution of an embodiment in the present invention. This apparatus is composed of an enzyme reactor 1 including an enzyme for converting AMP into ADP and an enzyme for converting ADP into ATP, a source 2 of AMP supply, a source 3 of phosphoric acid donator supply for converting AMP into ADP, a source 4 of phosphoric acid donator for converting ADP into ATP, variable fluid sending apparatus 5, 5' and 5" which are arranged and connected so that AMP and the above-described phosphoric acid donators are fed from each source 2, 3 and 4 of supply to an end of the enzyme reactor 1 to cause enzymic reactions and a reacting solution is flown out continuously from the other end, an automatic sampling apparatus 6 and an analyzing apparatus 7 for the reacting solution which are arranged and connected so as to automatically analyze ATP, ADP and AMP in the reacting solution flown out from the enzyme reactor 1, an arithmetical control apparatus 8 which is arranged and connected so as to control the amount of flowing in at least one of the above-described variable fluid sending apparatus 5, 5' and 5" by which arithmetical operation is carried out on the basis of data signals received from the above-described analyzing apparatus 7 and signals of the prescribed values previously fed so as to keep the ATP conversion in the above-described enzyme reactor 1 or the ATP concentration in the outlet of said reactor at a previously prescribed value, and a recovery apparatus 9 for recovering the reacting solution flowing from the enzyme reactor 1.

The enzyme reactor 1 may be any apparatus which satisfies the objects of the present invention. For example, the reactor 1 may be a column packed with the so-called immobilized enzyme which is obtained by immobilizing a suitable enzyme to a water-insoluble carrier by, for example, a chemical bonding process, an absorption process or an inclusion process (column type reactor). Useful water-insoluble carriers include polysaccharide derivatives such as cellulose, dextran or agarose, etc., vinyl polymer derivatives such as polystyrene, ethylene-maleic acid copolymer or cross-linked polyacrylamide, etc., polyaminoacids and polyamide derivatives such as L-alanine-L-glutamic acid copolymer or polyaspartic acid, etc., and inorganic derivatives such as glass, alumina or hydroxyapatite, etc., preferably polysaccharide derivative, inorganic derivatives such as glass and vinyl polymer derivatives such as polystyrene, and the preferred amount of such carriers used per the enzyme is 1 μg/enzyme unit to 100 g/enzyme unit (indicated by enzyme activity unit), more preferably 10 μg/enzyme unit to 10 g/enzyme unit.

It is also possible to use a so-called membrane type reactor wherein the inlet and the outlet of the reactor are partitioned by a membrane having fine openings through which reaction raw materials, solvent and reaction products can pass but enzymes cannot pass may be used. In these enzyme reactors, in view of operability and use over a long period of time, the column reactor is preferred as an enzyme reactor used in the present invention.

Enzymes present within the enzyme reactor 1 are composed of an enzyme for converting AMP into ADP and an enzyme for converting ADP into ATP. Phosphoric acid donators of the sources 3 and 4 of phosphoric acid donator supply are altered according to the kind of enzymes held in the reactor. Any combination of these enzymes and the phosphoric acid donators may be used, if it satisfies the objects of the present invention, and it is possible to use adenylate kinase (hereinafter referred to as AdK) as an enzyme for the reaction of converting AMP into ADP and ATP as a phosphoric acid donator, and acetate kinase (hereinafter referred to as AK) as an enzyme for the reaction of converting ADP into ATP and acetyl phosphate as a phosphoric acid donator. In this case, ATP is put in the source 3 and acetyl phosphate is put in the source 4.

When conversion enzymes: AdK and AK are used, it becomes possible to convert AMP or ADP into ATP, but such conversion is not put to practical use. Namely, it is necessary that these enzymes are those produced from microorganisms having an optimum growth temperature of 50° C. to 85° C. Examples of such microorganisms include microorganisms of the genus Bacillus such as *Bacillus stearothermophilus, Bacillus brevis, Bacillus coagulans, Bacillus thermoproteolyticus* or *Bacillus acidocaldarius*, etc., microorganisms of the genus Clostridium, microorganisms of the genus Thermoactinomyces, microorganisms of the genus Achromobacter, microorganisms of the genus Streptomyces, microorganisms of the genus Micropolyspora, microorganisms of the genus Thermus such as *Thermus aquaticus, Thermus thermophilus* or *Thermus flavus*, etc., microrganisms of the genus Thermomicrobium, etc. It is also possible to use other microorganisms which are grown at a normal temperature into which genes of the above-described microorganisms are introduced. Particularly, AdK and AK obtained from *Bacillus stearothermophilus* which is thermophiles well satisfy the objects of the present invention, because they do not easily lose their enzyme activity even if used for a long period of time, they are easily purified and they have a high specific activity. Other known combinations of the enzyme for converting ADP into ATP and the phosphoric acid donator, for example, polyphosphate kinase and polyphosphoric acid, creatine kinase and creatine phosphoric acid, and carbamate kinase and carbamyl phosphoric acid, etc., may be used. The source of the AMP supply is generally a container holding an aqueous solution of AMP having a suitable concentration. If necessary, it may be directly connected to another process for continuously producing AMP. For example, a line for separating and recovering AMP from a reaction product in the bioreactor in which ATP as an energy source is consumed to form AMP may be connected to the variable fluid sending apparatus 5 by means of a suitable means. The source 3 of phosphoric acid donator supply is generally in the form of a container holding a solution of phosphoric acid donator. When one of the enzymes in the enzyme reactor is AdK, a solution of ATP is put in the source 3 of phosphoric acid donator supply. This ATP may be comprised in part of ATP produced by using the aparatus for converting into ATP of the present invention.

Particularly, in the present invention, it is preferred to feed ATP of the source 3 of phosphoric acid donator supply to the enzyme reactor 1 together with AMP.

The source 4 of phosphoric acid donator supply is also generally a container holding a solution of phosphoric acid donator. For example, when the enzyme utilized is AK, a solution of acetyl phosphate is put in the container. The solution of acetyl phosphate easily decomposes at room temperature. Accordingly, when it is allowed to stand for a long period of time, it is preferable to add a means for keeping the temperature low (for example, 5° C. or less). The variable fluid sending apparatus 5, 5' and 5" may be comprised of any apparatus capable of varying the rate of flow by external control signals. For example, metering pumps driven by a pulse motor can be utilized. It is not always necessary that the apparatus 5, 5' and 5" are each individual pumps. In general, any pump may be used if it can feed solutions in the sources 2, 3 and 4 at independently controlled rates of flow.

Figure 2:
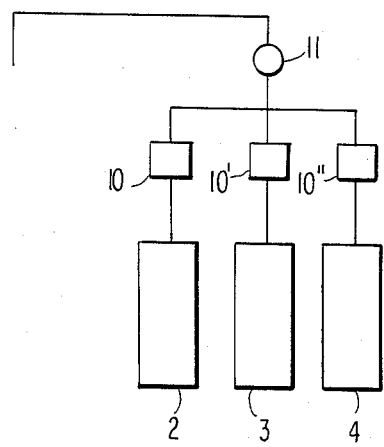
FIG. 2 is a schematic view showing another embodiment of the variable fluid sending apparatus of FIG. 1.

An example of one embodiment of a pump utilized for such a purpose is shown in FIG. 2. In FIG. 2, solutions in the sources, 2, 3 and 4 are fed respectively to the reactor 1 (not shown in FIG. 2) through automatic control valves 10, 10' and 10" by means of a pump 11. Further, the rates of flow passing through the automatic control valves 10, 10' and 10" are controlled by controlling the degree of opening and closing of the valves simultaneously by controlling the rate of flow of the pump 11 by external signals. Further, for example, electromagnetic valves may be used as the valves 10, 10' and 10". In this case, control may be carried out by repeatedly opening and closing, at short intervals of time, and varying the ratio of the time of being in an opened state to the time of being in closed state. There are a number of variations of possible embodiments, and any means may be used in short, if the solution in the feed sources 2, 3 and 4 can be sent to the reactor 1 in independent flow rates.

In order to automatically analyze the reacting solution which flows out from the enzyme reactor 1, it is most preferred to use a high performance liquid chromatographic apparatus. Although this apparatus has the drawback that only intermittent step information can be obtained because measurement of one sample requires several minutes to several tens of minutes, precision of measurement is the best with respect to quantitative analyses of ATP, ADP and AMP. Further, in the apparatus of the present invention, it is possible to sufficiently control an operation of the apparatus by data (each concentration of AMP, ADP and ATP) of one time per several minutes to several tens of minutes which is obtained by a high speed performance chromatographic apparatus. The automatic sampling apparatus for the reacting solution may be an autosampler for a high performance liquid chromatographic apparatus available on the market, which is connected to the line from reactor 1. Signals from the analyzing apparatus 7 are sent to the arithmetic control apparatus 8, where concentrations of ATP, ADP and AMP are calculated and signals for controlling the rate of flow in at least one of the above-described variable fluid sending apparatus 5, 5' and 5" are sent so as to keep the ATP concentration or the ATP conversion at a prescribed value. The arithmetic control apparatus 8 may be a microcomputer. When controlling the ATP conversion to the desired value, other data necessary for calculating the ATP conversion such as concentrations of each reaction raw material, etc., if they are constant, can be pre-set in the microcomputer. When the concentrations vary, an automatic sampling apparatus (not shown in FIG. 1) is provided on the inlet of the reactor 1, by which analysis is carried out by sampling from the inlet and the result of analysis can be utilized. The recovery apparatus 9 is used for recovering the reacting solution flowing from the reactor 1. The ATP concentration or the ATP conversion of the recovered solution is sufficiently controlled, and it may safely be said that nearly 100% conversion into ATP is substantially attained. However, hydrolyzed products of the phosphoric acid donator are included in addition to ATP. When the enzymes are AdK and AK, reactions in the reactor 1 proceed as follows.

(1)

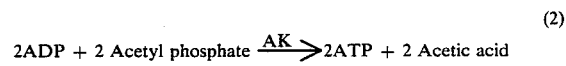

(2)

Accordingly, in this case, acetic acid is included in the reacting solution together with ATP. For the use in which presence of acetic acid does not cause trouble, the reacting solution recovered from the recovery apparatus 9 can be used as is, or after suitably controlling the concentration. When removal of acetic acid is required, it may be used after carrying out separation and purification by suitable means, for example, utilization of ion-exchange resin or activated charcoal.

AMP fed from the source 2 of the AMP supply in the apparatus of the present invention need not be pure, and it may be a mixture with ADP or ATP or it may contain materials which do not disturb the enzymic reactions in the reactor 1. The above-described reaction formulae (1) and (2) clearly show that all AMP and ADP can be converted into ATP in the end by suitably controlling the rate of flow in the fluid sending apparatus 5, 5' and 5". Further, only ADP which does not contain AMP or a mixture of ADP and ATP may be used. Namely, it can be used as an apparatus for converting ADP into ATP.

When used only for converting ADP into ATP, it is possible to use an apparatus which is the result of modifying the above-described apparatus of the present invention. Such a modified apparatus is more economically advantageous. The modification involves three points shown in FIG. 1, namely, (a) the enzyme reactor 1 is changed into "an enzyme reactor holding an enzyme which converts ADP into ATP", (b) the source 2 of AMP supply is changed into a source of ADP supply and (c) the source 3 of phosphoric acid donator for converting AMP into ADP is removed. Other constitutions are the same as those described in FIG. 1.

According to the apparatus of the present invention, conversion from AMP or ADP can be effectively carried out and ATP conversion can be kept at substantial 100% over a long period of time. Further, as the starting material converting into ATP in the apparatus of the present invention, it is not necessary to use pure AMP. However, a mixture of AMP with ADP or ATP may be used and ADP or a mixture of ADP with ATP may be used. This fact is very advantageous when applied industrially.

According to the present invention, ATP having high purity (substantially 100%) can be continuously produced at a moderate price by conversion of AMP or ADP. Accordingly, it is likely to be used more and more in the future as an energy source for bioreactors and as medicines which have been chiefly used hitherto.

In the following, the present invention is illustrated in detail with reference of examples.

EXAMPLES 1-4

As AdK and AK, samples produced from available *Bacillus stearothermophilus* (sold by Seikagaku Kogyo Co.) were used.

These two types of enzymes were immobilized on Sepharose 4B as follows. Namely, after 5 g of activated CH-Sepharose 4B (produced by Pharmacia Fine Chemicals) was washed to swell, 2,000 units of AK were added thereto to carry out the reaction, by which 1,000 units of immobilized AK were obtained. Likewise, 100 units of immobilized AdK were obtained from 250 units of AdK. A column (designated as 1 in FIG. 1) for reproduction of ATP (inside diameter: 1.6 cm, length: 10 cm) was packed with the immobilized AK and the immobilized AdK, and each substrate (AMP, ATP or acetyl phosphate) (designated as 2, 3 and 4, respectively, in FIGS. 1 and 2) dissolved in a 25 mM imidazole hydrochloride buffer solution containing 10 mM of magnesium chloride (pH 7.5) was fed to the column at a flow rate of 150 ml/hour. The reaction temperature in the column was kept at 30° C. Variable fluid sending apparatus (designated as 5 in FIG. 1) composed of a pulse pump (designated as 11 in FIG. 2) and an electromagnetic valve (designated as 10, 10' and 10'' in FIG. 2) were provided on the column, and control of them was carried out by a microcomputer (designated as 8 in FIG. 1). Further, samples of the solution flown out from the column were taken by an automatic sampling apparatus (designated as 6 in FIG. 1) and concentrations of AMP, ADP and ATP in the reacting solution flowing from the column were determined intermittently (at intervals of 15 minutes) by a high performance liquid chromatographic apparatus (produced by Waters Associates; column: μ Bondapak $C_{18}$, eluant: 50 mM phosphoric acid buffer solution (pH 6.0), and detection wavelength: 260 nm) (designated as 7 in FIG. 1). The reacting solution flown out of the column which was not sampled was recovered in the recovery apparatus (designated as 9 in FIG. 1). Further, the concentration of AMP was fixed to 1.5 mM and the concentration of acetyl phosphate was fixed to 5 mM.

The conversion to ATP was determined with varying concentration in the outlet to 0.063 mM ATP (ratio by concentration of ATP to AMP was 0.042; Examples 1), 0.07 mM ATP (ratio by concentration of ATP to AMP was 0.047; Example 2), 0.13 mM ATP (ratio by concentration of ATP to AMP was 0.087; Example 3) and 0.19 mM ATP (ratio by concentration of ATP to AMP was 0.127; Example 4) by a microcomputer.

As a result, after being fed to the column, AMP was not detected after only 20 minutes, and 98.5% of ATP and 1.5% of ADP were detected.

EXAMPLE 5

After the reaction was initiated under the same condition as in Example 2, quantitative analysis of the eluate from the column after 20 minutes was carried out by a high performance liquid chromatographic apparatus. On the basis of the result of determination, signals were fed to a variable fluid sending apparatus from the microcomputer, and the eluate from the column was sent back to the inlet of the column for reproduction of ATP in only an amount of 0.07 mM as ATP (0.047 based on the concentration of AMP) to circulate, while feeding of the initial ATP was stopped.

As a result, after the eluate from the reactor was used instead of ATP, ATP was kept in the range of 98% to 98.5% over 5 hours after 20 minutes.

EXAMPLE 6

A glass column having an inside diameter of 2.0 cm and a length of 12 cm was packed with 2,000 units of immobilized AK and 200 units of immobilized AdK obtained by the same method as in Example 1, and 3.0 mM of AMP, 0.13 mM of ATP (ratio by concentration of ATP to AMP was 0.043) and 10 mM of acetyl phosphate which were dissolved in a 50 mM imidazole hydrochloride buffer solution containing 25 mM of magnesium chloride and 0.04% of sodium azide having a pH of 7.5 were fed to the column at a flow rate of 300 ml/hour.

As a result, the conversion to ATP was kept in the range of 98.5% to 99.0% over 10 days after initiation of the reaction.

EXAMPLE 7

After the reaction was initiated under the same condition as in Example 6, an eluate from the column after 30 minutes (containing 98% of ATP) was circulated and fed to the column by the same manner as in Example 5 instead of ATP so that the ratio by concentration of ATP to AMP was 0.043.

As a result, the conversion to ATP was kept in the range of 98.2 to 98.7% over 10 days after initiation of the reaction.

EXAMPLE 8

A column having an inside diameter of 1.6 cm and a length of 10 cm was packed with 400 units of immobilized AK obtained by the same method as in Example 1, and 8 mM of ADP and 25 mM of acetyl phosphate which were dissolved in a 25 mM imidazole hydrochloride buffer solution containing 10 mM of magnesium chloride and 0.04% of sodium azide (pH:7.5) were fed to the column at a flow rate of 200 ml/hour. The same apparatus for reproduction of ATP as in Example 1 was provided on this column.

As a result, after feeding substrates to the column, 98.5% of ATP and 1.5% of ADP were detected after only 20 minutes, and thereafter a stabilized state was kept over 20 days.

While the invention has been described in detail and with reference to specific embodiments thereof, it will be apparent to one skilled in the art that various changes and modifications can be made therein without departing from the spirit and scope thereof.

What is claimed is:

1. An apparatus for converting AMP into ATP comprising:

(a) an enzyme reactor having outlet conduit means and inlet conduit means, wherein said enzyme reactor contains:
  (1) an enzyme which converts AMP into ADP, wherein said enzyme has been produced from microorganisms having an optimum growth temperature of 50° C. to 85° C., and also contains
  (2) an enzyme which converts ADP into ATP, wherein said enzyme has been produced from microorganisms having an optimum growth temperature of 50° C. to 85° C.;
(b) a source of AMP, wherein said source is connected to said enzyme reactor by said inlet conduit means;
(c) a source of phosphoric acid donator for converting AMP into ADP, wherein said source is connected to said enzyme reactor by said inlet conduit means;
(d) a source of phosphoric acid donator for converting ADP into ATP, wherein said source is connected to said enzyme reactor by said inlet conduit means;
(e) at least one variable fluid sending apparatus connected between each of said sources (b), (c) and (d), and said enzyme reactor, wherein at least one of said variable fluid sending apparatus controls the flow of AMP from said source of AMP (b), the flow of phosphoric acid donator from said source of phosphoric acid donator (c) and the flow of phosphoric acid donator from said source of phosphoric acid donator (d), into said enzyme reactor;
(f) a recovery apparatus connected to said enzyme reactor outlet conduit means through;
(g) an automatic sampling apparatus;
(h) an analyzing apparatus which analyzes the concentrations of ATP, ADP and AMP in the reaction solution flowing from said enzyme reactor, wherein said analyzing apparatus provides signals indicative of said concentrations to;
(i) an arithmetical control apparatus which on the basis of signals received from said analyzing apparatus (h) and signals of previously prescribed values stored therein, provides signals to at least one of said variable fluid sending apparatus (e) to control the amount of flow from said sources (b), (c) and (d) to said enzyme reactor so as to maintain the ATP conversion in said enzyme reactor or the ATP concentration in said enzyme reactor outlet conduit means at previously prescribed values.

2. An apparatus according to claim 1, wherein the enzyme and the phosphoric acid donator for converting ADP into ATP are acetate kinase and acetyl phosphate, respectively, and the enzyme and the phosphoric acid donator for converting AMP into ADP are adenylate kinase and ATP, respectively.

3. An apparatus according to claim 1, wherein the enzyme reactor is a column packed with enzymes immobilized to water-insoluble carriers.

4. An apparatus according to claim 1, wherein the analyzing apparatus is a high performance liquid chromatographic apparatus.

5. An apparatus for converting ADP into ATP comprising:
(a) an enzyme reactor having outlet conduit means and inlet conduit means, wherein said enzyme reactor contains:
  (1) an enzyme which converts ADP into ATP, wherein said enzyme has been produced from microorganisms having an optimum growth temperature of 50° C. to 85° C.;
(b) a source of ADP, wherein said source is connected to said enzyme reactor by said inlet conduit means;
(c) a source of phosphoric acid donator for converting ADP into ATP, wherein said source is connected to said enzyme reactor by said inlet conduit means;
(d) at least one variable fluid sending apparatus connected between each of said sources (b) and (c) and said enzyme reactor, wherein at least one of said variable fluid sending apparatus controls the flow of ADP from said source of ADP (b) and the flow of phosphoric acid donator from said source of phosphoric acid donator (c) into said enzyme reactor;
(e) a recovery apparatus connected to said enzyme reactor outlet conduit means through;
(f) an automatic sampling apparatus;
(g) an analyzing apparatus which analyzes the concentrations of ATP, ADP and AMP in the reaction solution flowing from said enzyme reactor, wherein said analyzing apparatus provides signals indicative of said concentrations to;
(h) an arithmetical control apparatus which on the basis of signals received from said analyzing apparatus (g) and signals of previously prescribed values stored therein, provides signals to at least one of said variable fluid sending apparatus (d) to control the amount of flow from said sources (b) and (c) to said enzyme reactor so as to maintain the ATP conversion in said enzyme reactor or the ATP concentration in said enzyme reactor outlet conduit means at previously prescribed values.

6. An apparatus according to claim 5, wherein the enzyme and the phosphoric acid donator for converting ADP into ATP are acetate kinase and acetyl phosphate, respectively.

7. An apparatus according to claim 5, wherein the enzyme reactor is a column packed with an enzyme immobilized to a water-insoluble carrier.

8. An apparatus according to claim 5, wherein the analyzing apparatus is a high performance liquid chromatographic apparatus.

* * * * *